US010315055B2

(12) United States Patent
Wheeler

(10) Patent No.: US 10,315,055 B2
(45) Date of Patent: Jun. 11, 2019

(54) TREATMENT OF PROSTATE CANCER USING ENHANCED ENERGY APPLICATION (EEA) IN HIGH INTENSITY FOCUSED ULTRASOUND (HIFU) PROCEDURES

(71) Applicant: Ronald E. Wheeler, Sarasota, FL (US)

(72) Inventor: Ronald E. Wheeler, Sarasota, FL (US)

( * ) Notice: Subject to any disclaimer, the term of this patent is extended or adjusted under 35 U.S.C. 154(b) by 245 days.

(21) Appl. No.: 15/139,841

(22) Filed: Apr. 27, 2016

(65) Prior Publication Data

US 2017/0312550 A1 Nov. 2, 2017

(51) Int. Cl.
*A61N 7/02* (2006.01)
*A61B 34/10* (2016.01)
*A61N 7/00* (2006.01)
*A61B 90/00* (2016.01)

(52) U.S. Cl.
CPC .............. *A61N 7/02* (2013.01); *A61B 34/10* (2016.02); *A61B 90/37* (2016.02); *A61B 2034/107* (2016.02); *A61B 2090/374* (2016.02); *A61B 2090/3782* (2016.02); *A61N 2007/0004* (2013.01)

(58) Field of Classification Search
CPC .............. A61N 7/02; A61N 2007/0004; A61N 2007/025; A61N 2007/027; A61N 2007/0043; A61N 2007/0047; A61B 34/10; A61B 2034/107; A61B 2090/374; A61B 2090/3782; A61B 90/37; A61B 2018/00547; A61B 2018/00904; A61B 2018/00994
USPC .................... 606/41; 607/96; 601/3; 600/411
See application file for complete search history.

(56) References Cited

U.S. PATENT DOCUMENTS

| 6,315,741 | B1 | 11/2001 | Martin et al. |
| 6,488,639 | B1 | 12/2002 | Ribault et al. |
| 8,727,987 | B2 | 5/2004 | Chauhan |
| 2007/0010805 | A1 * | 1/2007 | Fedewa ................ A61N 7/02 606/27 |

(Continued)

OTHER PUBLICATIONS

Ahmed, Hashim U. et al; Focal Ablation Targeted to the Index Lesion in Multifocal Localised Prostate Cancer: a Prospective Development Study; European Urology 68; pp. 927-936; 2015.

(Continued)

*Primary Examiner* — Thomas A Giuliani
(74) *Attorney, Agent, or Firm* — Charles S. Sara; DeWitt LLP

(57) ABSTRACT

HIFU treatment of localized prostate cancer includes identifying the cancer locations in a patient's prostate and visually segmenting the patient's prostate into areas for analysis and treatment. The section including the most aggressive cancer is determined to be the primary area and subjected to a first full HIFU treatment for a period intended to ablate the cancer. HIFU treatment is then stopped on the primary area, allowing it to rest, while simultaneously subjecting the next contiguous area of the prostate to HIFU treatment to ablate any additional areas of suspected cancer. HIFU treatment is then stopped in the contiguous area. The primary area is then subjected to a second full HIFU treatment for a period sufficient to ensure the complete ablation of the cancerous tumor. Repeating alternating full HIFU treatment on subsequent contiguous areas of the prostate ensures the complete ablation of any cancerous tumors in the prostate.

6 Claims, 2 Drawing Sheets

(56) References Cited

U.S. PATENT DOCUMENTS

2008/0091124 A1   4/2008  Fedewa et al.
2008/0269163 A1  10/2008  Sostaric et al.
2009/0099487 A1   4/2009  Chaluisan et al.
2013/0282040 A1  10/2013  Jun
2014/0378832 A1  12/2014  Sanghvi et al.

OTHER PUBLICATIONS

Cordeiro, Ernesto et al; Focal High-intensity Focused Ultrasound Targeted Hemiablation for Unilateral Prostate Cancer: A Prospective Evaluation of Oncologic and Functional Outcomes; European Urology 69 (2); pp. 214-220; 2016.

Dickinson, Louise et al; Image-directed, tissue-preserving focal therapy of prostate cancer: a feasibility study of a novel deformable magnetic resonance-ultrasound (MR-US) registration system; BJU International 112(5); pp. 594-601.

Ablatherm® User's Manual.

Chaussy et al., Current Urology Report: Table 1, High Intensity Focused Ultrasound: Efficacy summary; Robotic High Intensity Focused Ultrasound for Prostate Cancer: What Have We Learned in 15 years of Clinical Use?; Springer Science + Business Media, LLC 2011.

Nguyen et al., The Survival Benefit of Prostatectomy in Metastatic Prostate Cancer, Presentation made at the Southeaster Section Meeting of the AUA (Circa 2012—USC).

* cited by examiner

TREATMENT OF PROSTATE CANCER USING ENHANCED ENERGY APPLICATION (EEA) IN HIGH INTENSITY FOCUSED ULTRASOUND (HIFU) PROCEDURES

BIBLIOGRAPHY

Complete bibliographical citations to the documents cited herein can be found in the Bibliography, immediately preceding the claims.

FIELD OF THE INVENTION

The present invention is directed to the treatment of prostate cancer. The present invention is specifically directed to the treatment of prostate cancer utilizing an application of additional energy delivered with a single treatment using High Intensity Focused Ultrasound (HIFU).

BACKGROUND

Over the past twenty-five years, HIFU has been available primarily in Europe, Japan and England and to a lesser extent in other areas including but not limited to the Caribbean, Canada, South America, Australia, Russia and Ukraine. The HIFU process delivers a large amount of thermal energy to a confined space. This energy heats tissue to ablative levels while minimizing the effect on surrounding structures. Patients treated for prostate cancer with HIFU face significant adverse events that may also be present with other treatment modalities. A list of adverse events include primarily impotency, incontinence of urine, bowel injury, inability to kill all the cancer and urinary tract stricture or bladder neck contracture. The inability to validate a cure rate of better than 84% at greater than 5 years as well as a generalized recommendation to avoid the treatment of aggressive prostate cancer (arguably 35-40% of all prostate cancers) with HIFU invites a closer evaluation of the therapy and the protocol recommended by the manufacturer including all such therapies from EDAP™ (EDAP, International Corporation, Lyon, France), Sonacare™ (Focus Surgery, Indianapolis, Ind.) and Insightec™ (Taret Carmel, Israel) utilized heretofore in clinical practice or in research application.

At risk is the need to treat a patient a second time (using a reduced total energy measured in watts than the primary treatment), decreased ability to dissipate the energy due to a loss of tissue from the first treatment as well as compromised vascularity, a second anesthesia, loss of work time including a need to recuperate a second time, a potentially greater risk of adverse events (discussed below) as well as additional financial considerations involved in pre-operative costs, loss of business productivity and additional fixed costs for a second HIFU procedure including additional fees for all physicians involved as well as a technical component.

SUMMARY OF THE INVENTION

The present invention is directed to a method for HIFU treatment of localized prostate cancer in a patient, comprising identifying the location of an index lesion in a patient's prostate; visually segmenting the patient's prostate into areas for analysis and treatment, wherein the section including the index lesion is determined to be the primary area; subjecting the primary area of the patient's prostate to a first full HIFU treatment for a period sufficient to ablate the index lesion; stopping HIFU treatment on the primary area and allowing the primary area to rest while simultaneously subjecting the next contiguous area of the patient's prostate to a first HIFU treatment; and stopping HIFU treatment on the next contiguous area and allowing the next contiguous area to rest while subjecting the primary area to a second full HIFU treatment for a period sufficient to ensure the complete ablation of the index lesion. The method further includes repeating alternating full HIFU treatment processes on subsequent contiguous areas of the patient's prostate to ensure the complete ablation of any cancerous tumors in the patient's prostate.

With the present invention, men with prostate cancer are assured of an extended treatment with an improved treatment protocol that allows for the total comprehensive thermal ablation of the prostate (vastly different than the predecessor) and a predictable cure under a single anesthesia assuming certain patient selection criteria are met. Cure is defined by an absence of Prostate Specific Antigen (PSA) in organ confined disease concurrent with a negative Multi-Parametric Magnetic Resonance Imaging (MP-MRI) scan (preferred) or negative biopsy, status post treatment. In effect, men who are selected properly can expect to be cured in a single treatment session as the prostate will have received an enhanced energy application (EEA) essentially doubling the energy applied while allowing for the total death of all prostate cells associated with organ confined disease. This has proven to be a seminal discovery in medicine and will be proven to be a quantum leap in the understanding for the timing of cancer treatment, patient selection, best practice patterns and cure. In effect, the additional energy implemented allows cancers that were undertreated heretofore to now be treated effectively based on the ability to improve tissue penetration while doubling the acoustic ablative energy applied.

The present invention (EEA) shows no increase in adverse events when compared to any single pass of energy associated with the present treatment protocol performed by others around the world. The distinct advantage with EEA, however, is in knowing tissue with greater density, i.e., a more aggressive cancer, has now received appropriate, proven energy with an expected cure assuming a PSA level clinically was never higher than 8.5 ng/ml, determined by the inventor to be the "sweet spot." It is noted that validation (as evidence) for a lack of cancer within the prostate capsule (post treatment with HIFU using EEA) is a PSA nadir less than 0.30 ng/ml or a 3.0 T Multi-parametric MRI scan while many will still use a biopsy albeit not recommended due to a high percentage false negative results and therefore inconclusive.

Clinical destruction of tissue treated a second time during the same treatment cycle or event is unique, unusual and never part of a HIFU procedure performed anywhere in the world. The concern for any treating physician would be enhanced risk of adverse events to a patient and the uncertainty in outcome resulting from adding additional energy (tantamount to treating the gland tissue twice at a single setting). Moreover, the concern includes untoward risk or harm to the patient for the unknown as well as an enhancement of adverse events noted earlier including but not limited to impotency, incontinence, rectal wall injury (fistula) or urethral stricture. The thermal effects are directly related to the tissue temperature as it reaches or exceeds the destruction threshold.

In the annals of HIFU, the thought of adding additional energy to a patient's prostate gland identical to the use of a patented energy distribution protocol in the same setting has never been considered a viable option based on the applied physics. Plausible reasons as to why additional energy was never considered is based on a vast number of cases performed (approximating 40,000 cases), where the results showed essentially the same success rate as is commonly achieved with radical prostatectomy or about a 70% cure rate in excess of 5 years (Chaussy et al.). The scientific bench marks used to validate cure rate can be prioritized to Biochemical Disease Free Rates (BDFR) as best, absence of disease on a 3.0 T MP-MRI scan (second best albeit equally effective) or a repeat biopsy (third best albeit with significant patient risks including hospitalization from sepsis (8%) or death from septic shock; unknown but believed to be less than 2%) as well as extraordinarily high false negative rates secondary to biopsy bias. Additional plausible reasons EEA may not have been considered were associated with concerns for enhanced scarring or a greater intensity and frequency of adverse events (morbidity) including but not limited to damage to the neurovascular bundle (NVB)—resulting in impotency, damage to the sphincter mechanism allowing an involuntary loss of urine—called incontinence, concern for rectal wall injury causing a devastating recto-urethral opening or fistula, or the aforementioned urethral narrowing or tightening at the bladder neck from scar formation. Even though the side effect profile noted above is common for all other treatments, no one embraces the side effects (collectively) as acceptable.

An additional concern may involve a lack of academic enthusiasm and/or curiosity as to whether the acoustic energy application used in HIFU could in fact be validated to impact all prostate cancer subsets equally including low grade cancers (Gleason score: 3+3=6), intermediate grade cancers (Gleason score: 3+4=7 and possibly some 4+3=7 although many of this later group may be considered aggressive and finally very aggressive cancer comprised by Gleason scores of 4+4=8, Gleason scores of 4+5=9, Gleason scores of 5+4=9, and Gleason Scores of 5+5=10. To be sure, there has been no academic or research initiative to improve something that had been proven to be modestly successful at its current energy protocol. Heretofore, it was well known that forms of radiation therapy like Intensity Modulated Radiation Therapy (IMRT) and Proton Beam had success with low and intermediate grades of prostate cancer. Unfortunately, high grade, i.e., aggressive, prostate cancer rates of cure with IMRT and Proton Beam were unacceptable 35% and a 33% failure respectively at approximately 5 years post treatment, noted in a study comparative from Memorial Sloan Kettering (IMRT) and the University of Florida (Proton Beam) as presented at the Florida Medical Association meeting in 2015 while quoting these results in a medical forum. Upwards of 35-40% of all prostate cancers diagnosed are considered aggressive and would continue to pose an eminent threat to quality of life and life itself without this invention. Beyond being a potential public health issue, as an epidemic affecting quality of life, prostate cancer is most certainly a societal issue when consideration is given that all men will contract this disease if they live to be 100 years of age.

With rising healthcare costs dominating the world's market place, there is tremendous interest in cost saving concepts. It is well known that treating a patient a second time with any form of therapy adds to the morbidity while complicating the quality of life of those individuals exposed from such therapy. When outcome data from HIFU from around the world is evaluated there is a reproducible recurring trend where the more aggressive cancers are not cured despite the best intentions. What is known presently is that the density of cancer tissue for a Gleason 6 cancer is not the same as a Gleason 7 cancer which is not the same as a Gleason cancer 8-10. What is now known is that acoustic energy does not penetrate cancerous tissue equally or to the point of eradication or cell death due to greater density of tissue as the Gleason score rises. It has been reported in the literature (JAMA and Journal of Urology) that Gleason cancers of 8-10 have an 85% risk of recurrence within 5 years when Radiation or Radical Prostatectomy is performed.

While EEA associated with HIFU expects to change all of that, the current inability of acoustic energy to adequately penetrate all grades of prostate cancer or Gleason scores equally is similarly well known. Heretofore, the results from HIFU have been allowed to stand on their own with an understanding that HIFU likely will not work on higher grade disease prompting urologists like Stefan Thuroff, M.D. from Munich, Germany to prefer a radical prostatectomy to HIFU when a Gleason score of 8 is encountered. Until physicians are discouraged from treating all cancer with the same methodology without a clear rationale to do so, predictive failure is imminent. Inclusive to the previous comment, repeat HIFU procedures are commonly performed around the world when the initial therapy fails in accordance with a rising PSA value. Subsequent biopsy or a 3.0 T MP-MRI scan commonly validates the need to retreat. The typical protocol of energy delivery is 35-40 watts of power with a time to heat set at a certain time frame (in seconds) less than that noted in our EEA treatment and a cooling phase where the thermal energy is no longer being delivered allowing the heat to dissipate longer than that seen while using EEA protocol. This varies according to HIFU technology software utilized, but the concept of applying intermittent heat to the tissue is constant throughout the primary distribution of energy intended to cover the entire gland or part of a gland. Once the energy has been delivered to a preplanned treatment volume the case comes to a close.

The use of EEA demands a complete and comprehensive understanding of physics. Once acoustic energy is generated and targeted to tissue in a human being, it is imperative to have understood energy absorption as opposed to deflection (refractivity) and energy dissipation as opposed to energy intensification without dispersion. A significant element of risk and/or potential harm to a given patient was consciously interrogated and internalized until risk and abject harm dissipated and gave birth to the genius of harnessing intense energy to create opportunity. In regard to the present invention, once the first pass of energy delivery to the tissue is complete, a second pass commences alternatively thereafter, which is identical to the first pass, with no alteration of energy.

The present invention speaks to the presence of viable tissue or dying tissue that does not disintegrate in 30 minutes but rather remains to absorb the enhanced energy application while supplying an as yet functional blood supply; enough to allow for heat dispersion or dissipation precluding collateral damage from extraordinary heat build-up. This procedure when done systematically throughout the entire prostate including in the urethral area where cancer tissue has been shown to be present to varying degrees is highly effective. To be sure, while utilizing the present invention, a second pass (EEA) of energy is delivered after the first pass has been allowed to cool adequately as the subsequent block of tissue receives its first pass of energy (in a staggered format) dramatically enhancing the ability to cure a patient from prostate cancer due to the extraordinary understanding for the penetration of tissue with energy regardless of tissue density. In effect, the true threshold for tissue destruction has been redefined allowing for a greater percentage of patients being cured regardless of tissue cancer grade aggressiveness. The results are very promising, including a double digit advantage for cure in any comparison study imagined or selected. More importantly, when patient selection is improved and patients treat their cancer before the PSA rises above 8-8.5 ng/ml (regardless of Gleason grade or score), the cure rate of the disease treated with EEA becomes predictable with a Positive Predictive Value (PPV) for success approximating 98-99%. This compares favorably to the current treatment approach with a mean BDFR of 73.5% (Range: 57.3-84% at ≥22 months) seen throughout the world where second treatments are commonly performed at a mean rate of 37% (range: 18.7-78.4%).

Thus, the present invention does away with the need to treat a second time. It should be noted treating a patient a second time is complex and not without high risk to the patient for untoward adverse events not well calculated at the time of decision making due to poor image quality (comparatively speaking to a naïve case treatment) as well as an alteration in the time for energy delivery from 6 seconds on and 4 seconds off (de novo treatment) to 5 seconds on and 5 seconds off during a standard second treatment. The EEA process has a secondary benefit with an enhancement of survival in men who have incurable prostate cancer (Nguyen, M. M., et al) based on microscopic spread that is clinically unknown at the time of treatment to varying degrees when the PSA value is ≥8-8.5 ng/ml and/or when other diagnostic markers are suggestive of T3 or T4 disease or disease beyond the prostate capsule. When the entirety of the prostate is ablated (proven with EEA) or radical prostatectomy has been performed, the survival advantage to the patient increases versus the group that did not experience total ablation or extirpation (removal) of the gland consistent with when radiation was performed. To be sure, the ability to treat dense tissue (aggressive cancer) to the point of ablation enhances life expectancy to the benefit of all men in all societies with minimal to no complications.

The objects and advantages of the invention will appear more fully from the following detailed description of the preferred embodiment of the invention made in conjunction with the accompanying drawings.

DETAILED DESCRIPTION OF THE INVENTION

Figure 1:
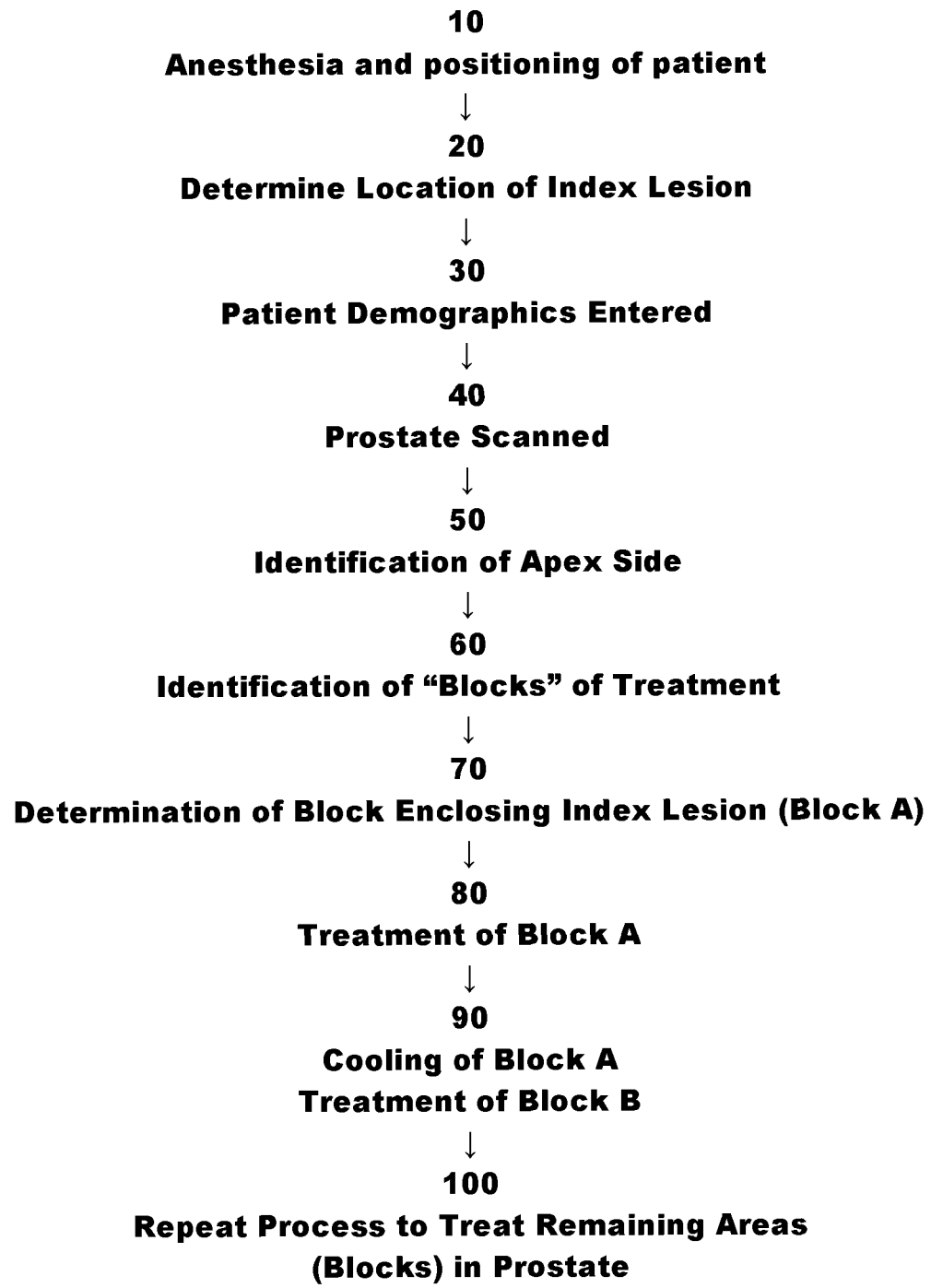
FIG. 1 is a flow chart showing the steps in the operation of the present invention.

For purposes of the present disclosure, the following abbreviations apply:
BDFR: Biochemical Disease Free Rates (Freedom from Disease)
EEA: Enhanced Energy Application
HIFU: High Intensity Focused Ultrasound
IMRT: Intensity Modulated Radiation Therapy
MP-MRI: Multi-parametric Magnetic Resonance Imaging
MRI: Magnetic Resonance Imaging
NVB: Neurovascular Bundle
PPV: Positive Predictive Value
PSA: Prostate Specific Antigen The process of the present invention involves a computer-controlled medical device for the treatment of localized prostate cancer. Representative devices useful for this procedure include the ABLATHERM® computer controlled device (EDAP TMS S.A., Vaulx-en-Velin, France) and the SONABLATE® medical device for treatment of prostate conditions. Reference is made to the ABLATHERM® User's Manual and U.S. Pat. No. 6,315,741 to Martin et al., which are incorporated herein by reference in their entirety, for a description of the HIFU process.

The HIFU medical device provides a HIFU procedure for ablation of prostate tissue. The ultrasound energy is delivered via an endorectal probe, which includes an imaging system. The ultrasound waves propagate through the rectal wall and are focused on a portion of the prostate, generating intense heat, upwards of 94° C., causing an intended ablation of tissue within the focal area. The device contains a treatment transducer, an endorectal ultrasound imaging transducer, and a cooling system that intends to protect the rectal wall during the procedure. The heat distribution within the prostate is concentrated at the focal point of the transducer, and the tissue is destroyed when a threshold temperature is reached. When power is maintained at the focal point, the lesion will continue to elongate itself. After each lesion is created, the transducer is repositioned to create the next lesion or block and the heating process is repeated.

The size of the lesion is dependent on the frequency, power level, and duration of the HIFU pulse. HIFU parameters are selected to optimize the size of the lesion, while preserving the rectal wall and the surrounding tissues.

Martin et al. describe the surgical methods using HIFU including the steps of prior to incising tissue of a surgery patient, applying ultrasonic energy at a combination of frequency, time of exposure and power intensity to cause controlled coagulation and necrotization of tissue in the patient such that a region of cauterized tissue is formed in the tissue at predetermined locations where the tissue is to be cut. A HIFU apparatus includes an ultrasound transducer device supported by a top arm, which is brought into contact with a tissue by an acoustic coupler. A bottom arm slips under the tissue and aids in fixing the distance between the transducer device and the tumor. The transducer device is activated and used to form a shell of coagulated and necrotized tissue around the tumor. Then, the transducer provides a focal region for attacking the legion. Continuous wave or post acoustic energy is applied for a predetermined time to necrotize the tissue of the sample.

Other suitable HIFU systems, which may be incorporated to execute the methods described herein are disclosed in U.S. patent publication 2008/0091124 to Fedewa et al, filed Oct. 23, 2007, U.S. patent publication 2014/0378832 to Sanghvi et al, filed Sep. 12, 2014, U.S. patent publication 2013/0282040 to June, filed Jun. 28, 2013, and U.S. Pat. No. 8,727,987 to Chauan, the disclosures each of which is expressly incorporated herein by reference.

An exemplary HIFU system is disclosed and illustrated in FIG. 1 of U.S. patent publication 2014/0378832 to Sanghvi et al, in which the HIFU system includes a probe having a transducer member, a positioning member, a controller operably coupled to the probe and the positioning member, a user input device (such as a keyboard, trackball, mouse and/or touch screen), and a display. The probe is operably connected to the controller through the positioning member. However, the probe may be directly connected with the controller. The positioning member is configured to linearly position the transducer member.

The process for conducting the invention, using the Ablatherm technology, is directed to the following steps according to the reference numbers in FIG. 1:

10: The patient is placed under general anesthesia. Once anesthetized, the patient is positioned on the treatment module in right lateral decubitus (RLD) position. An endorectal probe is inserted into the patient using a transrectal approach in an atraumatic manner.

20: The contours of the patient's prostate and the location of the index lesion are determined and located on a computer display. The index lesion is defined as the area of most aggressive cancer in the prostate. The index lesion is located by ultrasound imaging, in concert with and based upon a previous biopsy or a 3.0 Tesla Multi-parametric MRI scan.

30: The patient demographics are entered into the computer database identifying name, date of birth, standard treatment protocol, radiation failure, repeat HIFU and other criteria.

40: The prostate is scanned (robotically) and the volume is measured relating to height, width and length. This determines the area for treatment consideration.

50: An anatomical Apex identification, i.e., the true Apex, in the prostate gland is made and the lower limit for energy release is determined usually 4-8 mm cephalad to the true Apex.

Figure 2:
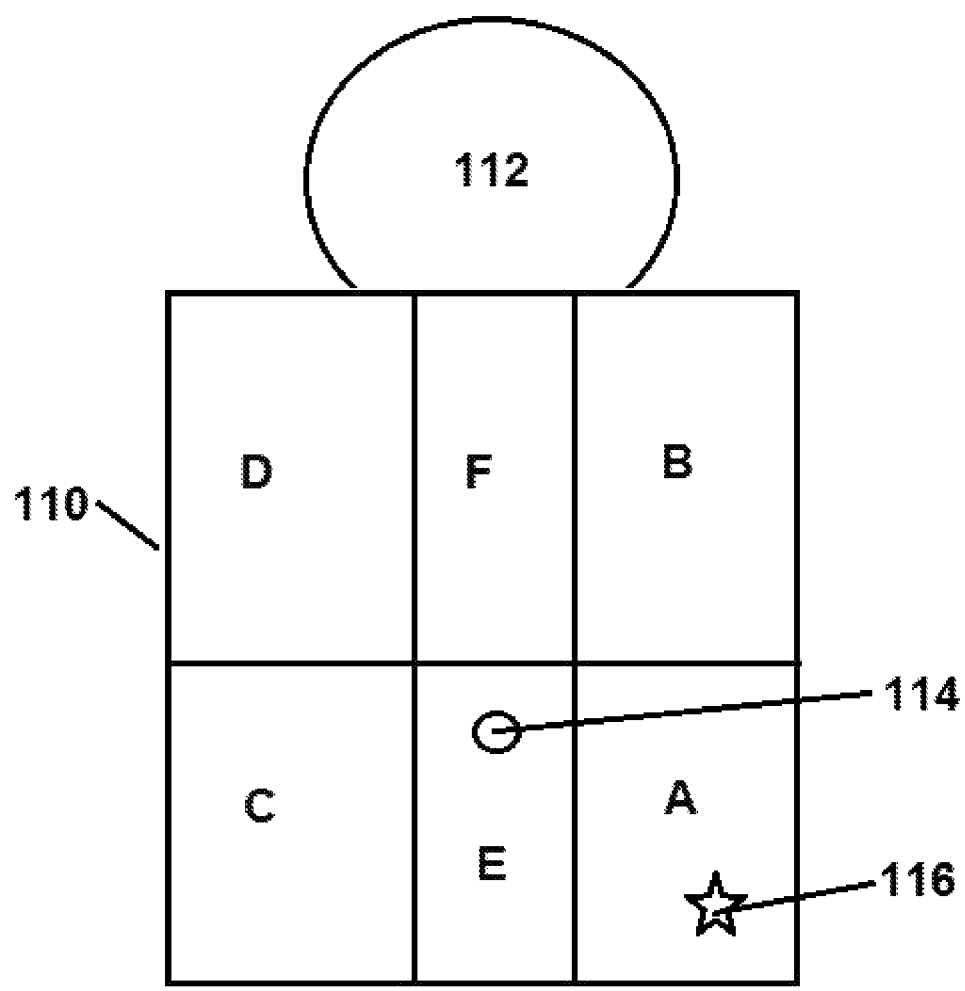
FIG. 2 is a schematic diagram of a prostate.

60: Coordinates are placed on the prostate gland to identify different areas (known as "Blocks") of treatment. Reference is made to FIG. 2, which schematically illustrates a prostate gland 110, positioned adjacent the patient's bladder 112. The urethral cavity 114 is illustrated as a reference point. Typically, the prostate gland 110 is computer-scanned into 6 sections or blocks. Each block is given a letter. Referring to FIG. 2, this are shown as Blocks A, B, C, D, E and F. The block containing the index lesion 116 will be referenced Block A. Block A will be in the Apex of the prostate.

70: In a typical treatment protocol, Block A in the prostate gland 110, i.e., the block with the index lesion 116, will be treated first. In this instance once Block A has been fully treated, Block B is treated, allowing Block A to cool. This treatment procedure is then duplicated, albeit adjusted for size as a resultant of heat applied previously, with respect to Blocks A and B, thereby giving each block two treatments with intervening cooling periods. This treatment protocol is then duplicated for the other blocks. A determination of the next set of blocks is decided by the practicing physician. However, the treatment process covers the apex-base block pair, i.e., Blocks A-B, Blocks C-D, Blocks E-F. For example, the treatment protocol is duplicated for Blocks C and D, and then Blocks E and F. In this manner, the entirety of the prostate gland 110, i.e., all blocks making up the prostate, is treated twice with alternating cooling.

80: Assuming Block A includes the index lesion 116, the protocol for treating Block A is as follows:
   a. Within Block A, the probe head moves robotically approximately 1.7 mm to each lesion until the targeted volume has been completely treated in Block A.
   b. Energy is generated through a 3 MHz focal point, at 80-94° C. for 6 seconds (heating) and off for four seconds (cooling), then moves to next lesion to completion.
   c. The focal distance to the intended gland is 45 mm from where the energy is generated (from the probe transducer) to the intended tissue where coagulative necrosis occurs following energy delivery (over time, usually days to weeks).
   d. The treatment zone is associated with a focal volume that varies based on technology or advancements but is most commonly 19-26 mm in Anterior-Posterior diameter and 1.7 mm in diameter (also known as a treating cigar). In essence, hundreds of shots are generated in treating a gland with great precision.

90: Once Block A has been treated, the probe head is then directed to Block B and the same treatment protocol described with respect to Block A is effected on Block B. Heat dissipation in Block A takes place based on absorption of energy by the tissue as well as a relative cooling from blood flow pattern present. In addition, the rectum is cooled with a cooling fluid, such as ABLASONIC cooling and coupling fluid (EDAP TMS, Vaulx-en-Velin, France), whereby the fluid goes through a chiller device keeping the rectal wall cool at 5° C., while ultrasound energy waves are transmitted as described above. Firing phases will be based on volume of the organ treated and based on user preference referencing an area to be treated. Firing phases or actual treatment sequences continue throughout the HIFU protocol consistent with several hundred acoustic shots (lesions) fired predictably over time or until the entire treatment plan has been carried out with respect to Block A.

100: This process is repeated until all of the treatment areas, e.g., all six Blocks A, B, C, D, E and F, have been treated.

Thus, the present invention is directed to the repeated HIFU treatment outlined above with respect to different treatment blocks, in reference to the prostate gland 110, all conducted in one procedure and under the same anesthesia. EEA has established that additional energy can be administered but only with great caution by an expert, fully qualified in imaging while having an equivalent understanding of physics relevant to heat absorption with tissue cavitation, heat dispersion or dissipation, blood flow and adequate rectal wall cooling. Additionally to the above description, additional blocks of tissue (3-5) are treated (depending on the size of the prostate) apex to base with the same description given 7-18 with adjustments made in the treatment protocol for size expansion or size reduction.

EXAMPLE

The following example is included solely to aid in a more complete understanding of the subject invention. The example does not limit the scope of the invention described herein in any fashion.

Improved Prostate Cancer Outcomes from HIFU Therapy Using MP-MRI Localization, EEA and Optimized Patient Selection Criteria: Early Results from a Pilot Program that Establishes a Much Improved Outcome while Using EEA Introduction & Objective:
To evaluate a retrospective patient population of 115 patients treated with HIFU from 2013-2015 in an effort to show unequivocally an ability to cure prostate cancer in an improved and predictable manner based on the use of EEA in a specified patient population. This study is expected to alter the way we treat prostate cancer more effectively and ensure outcomes double digits better than previously known.

Methods:
While 115 patients were identified, interest is noted in men with prostate cancer who presented with a PSA level of less than or equal to 8.5 ng/ml. This is the same theme used in Exhibit 1, allowing us to further validate a significant medical finding heretofore never seen with this level of excellence regardless of the treatment offered. 57 patients qualified and were selected from the total and evaluated for cure in cancers of aggression noted with a Gleason scores of 7, Gleason scores of 8 and Gleason scores of 9; as well as more commonly seen less aggressive Gleason scores of 6.

Results:

Regardless of Gleason score noted, EEA was applied in all instances noting a cure rate of 100% in this selected patient population at upwards of 3 years. Regardless of study evaluated and treatment therapy offered heretofore, there is no evidence to suggest this result is anything but spectacular, novel, and unique as well as a welcome invention to offer in an effort to improve the status quo in prostate cancer treatment failures by double digits. This measure of cure can only be attributed to the invention noted herein as EEA.

Complications:

There were no untoward complications associated with the significant addition of energy placed, noting this invention to be safe for all patients.

Conclusions:

EEA provides us with an incredible invention demonstrating an improved and more efficacious methodology whereby energy is placed noting a quantum leap in outcome data never seen before in more than 25 years of use. In effect the energy given to any given patient is essentially double the manufacturer's only recommendation, based primarily on an improved understanding of physics while understanding the very real possibility for irreversible harm to a patient if utilized. HIFU is a procedure that while successful (similar to other treatments offered) did not have the ability to cure an aggressive cancer in a single treatment session until EEA was invented and applied. This change in the energy delivery protocol, which could never be obvious for all reasons, is an enhancement of energy that has been shown to change dramatically the outcome for a procedure with a disease that virtually all men will acquire if they live long enough. Additionally, our discovery is not associated with any untoward effects beyond that seen in any primary treatment, a bonus to any invention. This invention will save millions of healthcare dollars by curing a disease decidedly at a much earlier time line avoiding a second treatment commonly seen with Radiation, Radical prostatectomy or HIFU performed without EEA. Finally, while we expect others to adopt this treatment protocol, this is the second study to show the benefit of patient selection but unique in that the entire group of patients were treated with EEA.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Chaussy, C. G. and S. F. Thuroff, "Current Urology Report: Table 1, High Intensity Focused Ultrasound: Efficacy summary; Robotic High Intensity Focused Ultrasound for Prostate Cancer: What Have We Learned in 15 years of Clinical Use?"; Springer Science+Business Media, LLC 2011

Nguyen, M. M., et al., "The Survival Benefit of Prostatectomy in Metastatic Prostate Cancer;" Presentation made at the Southeastern Sectional Meeting of the AUA (Circa 2012-USC)

ABLATHERM® User's Manual

U.S. Pat. No. 6,315,741 to Martin et al.

What is claimed is:

1. A method for HIFU treatment of localized prostate cancer in a patient, comprising:
   a. identifying a location of an index lesion in the patient's prostate, wherein the index lesion comprises an area of most aggressive cancer;
   b. visually segmenting the patient's prostate into areas for analysis and treatment, wherein a section including the index lesion is determined to be a primary area;
   c. subjecting the primary area of the patient's prostate to a first full HIFU treatment for a period sufficient to ablate the index lesion;
   d. stopping HIFU treatment on the primary area and allowing the primary area to rest while simultaneously subjecting a next contiguous area of the patient's prostate to a first HIFU treatment; and
   e. stopping HIFU treatment on the next contiguous area and allowing the next contiguous area to rest while subjecting the primary area to a second full HIFU treatment for a period sufficient to ensure the complete ablation of the index lesion during a same treatment cycle.

2. The method of claim 1 wherein identifying a location of an index lesion in the patient's prostrate comprises:
   a. placing the patient under general anesthesia;
   b. positioning the patient on a treatment module in right lateral decubitus (RLD) position;
   c. inserting an endorectal probe into the patient using a transrectal approach in an atraumatic manner; and d. determining a position of the patient's prostate and the location of the index lesion.

3. The method of claim 2 wherein the location of the index lesion is determined by a method selected from the group consisting of ultrasound imaging, a biopsy, and multi-parametric MRI scan.

4. The method of claim 1 further comprising subjecting the next contiguous area to a second HIFU treatment.

5. The method of claim 4 further comprising repeating alternating HIFU treatment processes on subsequent contiguous areas of the patient's prostate.

6. The method of claim 1 wherein the patient's prostate is visually segmented into 6 areas, wherein:
   a. the primary area of the patient's prostate is designated block A,
   b. a next contiguous area of the patient's prostate is designated block B,
   c. a next contiguous area of the patient's prostate is designated block C,
   d. a next contiguous area of the patient's prostate is designated block D,
   e. a next contiguous area of the patient's prostate is designated block E, and
   f. a next contiguous area of the patient's prostate is designated block F,
   wherein a pattern of treatment is as follows:

1. subjecting block A to the first full HIFU treatment for the period sufficient to effectively ablate the index lesion;
2. stopping treatment of block A while simultaneously subjecting block B to the first HIFU treatment;
3. stopping treatment of block B while performing the second full HIFU treatment on block A to ensure complete ablation of the index lesion;
4. stopping treatment of block A and performing the second HIFU treatment on block B;
5. stopping treatment of block B while simultaneously subjecting block C to a first full HIFU treatment;
6. stopping treatment of block C while simultaneously subjecting block D to a first full HIFU treatment;
7. stopping treatment of block D and performing a second full HIFU treatment on block C;
8. stopping treatment of block C and performing a second full HIFU treatment on block D;
9. stopping treatment of block D while simultaneously subjecting block E to a first full HIFU treatment;
10. stopping treatment of block E and subjecting block F to a first full HIFU treatment;
11. stopping treatment of block F and performing a second full HIFU treatment on block E;
12. stopping treatment of block E and performing a second full HIFU treatment on block F.

* * * * *